US009710614B2

(12) United States Patent
Ruzic et al.

(10) Patent No.: US 9,710,614 B2
(45) Date of Patent: Jul. 18, 2017

(54) PROCESS FOR THE AUTOMATED CLASSIFICATION AND ANALYSIS OF RAW DATA AND ITS USE IN THE OPTIMIZATION OF PROCESSES

(75) Inventors: Milos Ruzic, Celje (SI); Anica Pecavar, Novo Mesto (SI)

(73) Assignee: KRKA, TOVARNA ZDRAVIL (SI)

( * ) Notice: Subject to any disclaimer, the term of this patent is extended or adjusted under 35 U.S.C. 154(b) by 763 days.

(21) Appl. No.: 13/502,248

(22) PCT Filed: Oct. 15, 2010

(86) PCT No.: PCT/EP2010/006309
§ 371 (c)(1),
(2), (4) Date: Jul. 30, 2012

(87) PCT Pub. No.: WO2011/045073
PCT Pub. Date: Apr. 21, 2011

(65) Prior Publication Data
US 2012/0283959 A1    Nov. 8, 2012

(30) Foreign Application Priority Data

Oct. 16, 2009  (EP) .................................. 09013284

(51) Int. Cl.
| G06F 17/00 | (2006.01) |
| G01N 30/00 | (2006.01) |
| G06F 19/00 | (2011.01) |
| G01N 30/86 | (2006.01) |

(52) U.S. Cl.
CPC ....... *G06F 19/707* (2013.01); *G01N 30/8658* (2013.01); *G06F 19/703* (2013.01)

(58) Field of Classification Search
CPC .......... G01N 30/8658; G06F 17/30286; G06F 19/703; G06F 19/707; Y10S 707/99944; Y10S 707/99945
USPC ......... 702/22, 23, 127, 179, 196, 24, 25, 30; 706/47
See application file for complete search history.

(56) References Cited

PUBLICATIONS

International Search Report mailed Jan. 12, 2010 in PCT/EP2010/006309 filed Oct. 15, 2010.
International Preliminary Report on Patentability mailed Mar. 14, 2012 in PCT/EP2010/006309 filed Oct. 15, 2010.
Neuweger et al., "MeltDB: a software platform for the analysis and integration of metabolomics experiment data," Bioinformatics, 2008, vol. 24, No. 23, 2726-2732.
Huidobro et al., "Ultra rapid liquid chromatography as second dimension in a comprehensive two-dimensional method for the screening of pharmaceutical samples in stability and stress studies," Journal of Chromatography A, 2008, vol. 1190, 182-190.
Schoenmakers et al., "A protocol for designing comprehensive two-dimensional liquid chromatography separation systems," Journal of Chromatography A, 2006, vol. 1120, 282-290.

(Continued)

*Primary Examiner* — John H Le
(74) *Attorney, Agent, or Firm* — Hovey Williams LLP (57) ABSTRACT

A process for the automated classification and analysis of raw data includes the selection and use of a method suitable for analyzing the physical and chemical properties of materials such as chemical compounds. The results can then be used to optimize a process of interest, such as a chemical process. The chemical process may include a chemical reaction or a purification process including chemical and physical steps.

19 Claims, 7 Drawing Sheets

(56) References Cited

PUBLICATIONS

Ni et al., "Peak pattern variations related to comprehensive two-dimensional gas chromatography acquisition," Journal of Chromatography A, 2005, vol. 1086, 165-170.

Reichenbach et al., "Smart Templates for peak pattern matching with comprehensive two-dimensional liquid chromatography," Journal of Chromatography A, 2009, vol. 1216, 3458-3466.

PROCESS FOR THE AUTOMATED CLASSIFICATION AND ANALYSIS OF RAW DATA AND ITS USE IN THE OPTIMIZATION OF PROCESSES

RELATED APPLICATIONS

This application claims priority to PCT International Patent Application No. PCT/EP 2010/006309, filed Oct. 15, 2010, which claims the priority benefit of EP Patent Application No. 09013284.6, filed Oct. 16, 2009, both of which are hereby incorporated by reference in their entirety.

The present invention relates to a process for the automated classification and analysis of raw data, said process comprising the selection and use of a method suitable for analyzing the physical and chemical properties of materials such as chemical compounds, e.g. those used as active pharmaceutical substances. The results can then be used to optimize a process of interest, e.g. a chemical process such as a chemical reaction or a purification process including chemical and physical steps.

In the process of the present invention, the data obtained from the use of the analytical method are associated with suitable metadata (descriptive data). By using this metadata and suitable reference samples, analytical results obtained under varying experimental conditions can be correlated and analyzed automatically for parameters of interest, e.g. the effect of changes in the molar ratio of reactants used in a chemical synthesis such as the synthesis of a pharmaceutically active compound. The analysis is conducted by using multivariate analysis in a more efficient manner as compared to the prior art.

BACKGROUND OF THE INVENTION

Enterprise content management systems (ECMS) have been introduced in the regular workflow in the analytical, chemical and pharmaceutical industries which usually face a large amount of analytical data to be processed, properly assigned, structured and evaluated/analyzed. One of the goals of data processing and organization is to arrive at an arrangement of the data useful for applying multivariate methods of data analysis (MVA). This type of analysis is based on the statistical principle of multivariate statistics which involves observation and analysis of more than one statistical variable at a time.

Up to the present date, it has proven difficult to implement an automatic procedure for providing suitable arrangements of data for multivariate analysis. This is so because the results obtained in an analytical experiment, e.g. the relative retention times of peaks measured in an HPLC experiment (HPLC=High Pressure Liquid Chromatography), vary when the working parameters and conditions used in the experiment such as temperature, pressure, pH of solvents, e.g. the composition and pH of the mobile phase used in HPLC, are changed. Accordingly, the user of the analytical method has to manually organize the measured data and associate it with the attribute of interest of the sample analyzed. For example, in a measured assay of HPLC peaks, i.e. a chromatogram, which is an example of a specific set of data as discussed above, each HPLC peak has to be linked to a specific impurity, which is the attribute of interest in this specific case. This has to be done manually for each chromatogram measured which presents a significant workload. Other attributes of interest may be a specific colour, smell, particle size or particle size distribution, etc. The thus processed data could then be used for further analysis and optimization procedures.

It is an object of the present invention to provide a process which allows for the above type of analysis in a more efficient manner.

SUMMARY OF THE INVENTION

The above object is solved by the process as defined in claim 1. Specifically, the present invention provides a process for the automated classification and analysis of data such as raw data, said process comprising the following steps:

i) selecting an analytical method such as high pressure liquid chromatography (HPLC) for use in an analytical experiment;

ii) determining working parameters and conditions for the selected method, such as temperature or type and composition of an HPLC column, composition of an HPLC mobile phase, etc., which parameters and conditions have an effect on the results obtained by using the selected method;

iii) assigning to a set of data, said set of data including a) the type of the selected method and b) a specific combination of working parameters and conditions used in the analytical experiment, a unique analytical method code (Hash value);

iv) applying the method characterized by said Hash value to at least one reference sample and at least one or more further samples obtained from a process for preparing said samples, such as a chemical, pharmaceutical, physical or biochemical process such as in particular a process for synthesizing or purifying a chemical compound, in which process at least one parameter such as temperature, solvent, or ratio of reactants etc. is to be optimized;

v) storing the Hash value and the name of the sample as metadata together with the analytical results obtained in step (iv) as an analytical report;

vi) automatically extracting, e.g. by using an extraction template or another extraction process, the relevant metadata from the analytical reports (Hash value, sample name, etc.) and transferring them to an enterprise content management system (ECMS) or other database systems;

vii) automatically organizing the results according to the Hash value in the ECMS or any other suitable database system, viii) correlating the sets of data characterized by different Hash values on the basis of the reference sample measured for each Hash value, thereby creating a correlation matrix or table;

ix) using the correlation matrix or table for multivariate analysis of the one or more of the parameters of the process resulting in the samples recited in step (iv);

x) optionally, visualizing the results as one or more graphic charts;

xi) using the results of steps (ix) and, optionally, step (x) to optimize said one or more parameters of the process as defined in step (iv);

xii) optionally, verifying the process on the laboratory, pilot plant or industrial scale.

It is within the scope of the present invention to change the order of the process steps as listed above. However, preferably the process of the present invention is conducted in the order as stated above. Also, the process of the present invention may comprise additional steps to those stated hereinabove. In one embodiment, the process of the present invention consists of the steps as defined herein.

Further preferred embodiments of the present invention are defined in the dependent claims as originally filed, the subject-matter of which is incorporated by reference into the specific contents of the present description.

DETAILED DESCRIPTION OF THE INVENTION

In the following detailed description of the present invention, the following terms and definitions are used:

Analytical method means a chemical or physical method used for obtaining physical and/or chemical information on materials of interest. Examples of analytical methods for use in the present invention are chromatography such as liquid chromatography, in particular high pressure liquid chromatography (HPLC), gas chromatography, supercritical fluid chromatography, thin layer chromatography, electrophoresis, etc. . . . .

Working parameters and conditions of an analytical method are physical and chemical parameters which have an influence on the results obtained by using the analytical method. Examples are temperature, pressure, and type and composition of the agents used in the analytical method, e.g. the column materials used in HPLC or the composition and pH of the mobile phase used in HPLC etc.

An analytical method code or Hash value is a unique code assigned to a specific set of working parameters and conditions used in a specific analytical experiment, e.g. an HPLC experiment, which working parameters and conditions have an influence on the response signal measured in such experiment, e.g. the relative retention time and/or intensity of a peak measured in an HPLC experiment.

Each time the method or a working parameter or condition of the method is changed beyond a predetermined limit, a new analytical method code (Hash value) is assigned to the set of data (based on the type of method and the working parameters and conditions used) characterizing the experiment.

In particular, with regard to the use of HPLC as the analytical method, the Hash value is changed whenever the change of one of the following parameters exceeds the limits set out below:

the pH of mobile phase is changed for more than ±0.3;
the column temperature is changed for more than ±3° C.;
an additional organic modifier is introduced in the mobile phase;
another organic modifier is used (e.g. methanol vs. acetonitrile);
the slope of gradient profile is modified for more than ±2%;
percentage of organic solvent in the mobile phase is changed for more than ±1%;
the column is exchanged for another with different selectivity type (e.g. C18 vs. phenyl, etc.).

Also, when a change in one of the following parameters
stationary phase (type and manufacturer)
composition of mobile phase: (buffer—pH and ionic strength; organic modifier—type and proportion)
column temperature
causes a change in the relative retention times (retention factor ($k=(t_R-t_0)/t_0$)) of more than ±5%, the method code has to be changed.

In this context, it is noted that the relative retention ($\alpha=k_2/k_1$) is a chemical/thermodynamic variable that does not depend on the physics of the column. In this context, it is noted that physics of the column relates to the dimensions of the column such as column length, column diameter and particle size of stationary phase. These parameters have an effect on the retention times but not on the relative retention times.

A reference sample means a material such as the reaction mixture of a chemical synthesis or the crude product which will show in an analytical experiment all the properties of interest e.g. the presence of characteristic components such as by-products and impurities. In other words, reference samples are standard reaction products or crude or purified samples prepared according to some route of synthesis and having an impurity profile which is representative for that route of synthesis.

For example, in case the reference sample is a crude product, said crude product will show in an analytical experiment such as HPLC peaks for all (standard) impurities of interest. In case of a reaction mixture, it will show peaks for the reactants, intermediates, by-products and the product of interest.

One or more further samples as recited in step (iv) of the process of the invention means samples made by using a process which differs from that used to make the reference sample. For example, with regard to a process for synthesizing a chemical compound, the difference(s) is/are based on varying the synthesis process parameters while the route of synthesis as such is not changed. This is explained in more detail below.

For example, in case the reference sample is a crude product prepared in the own laboratory or obtained from a commercial source, a further sample will be one which has been subjected to, for example, an additional purification step, e.g. by contacting the crude product with a suitable solvent.

In case a reaction mixture is used as the reference sample, the further sample will be the product of the reaction conducted by varying at least one parameter as compared to the preparation of the reaction mixture forming the reference sample, e.g. the molar ratio between the reactants or the concentration and amount of solvent used in the reaction may be varied.

A process for preparing a sample can be a chemical, pharmaceutical, physical or biochemical process. Examples of specific processes are the chemical synthesis of a specific pharmaceutically active ingredient, the preparation of suitable pharmaceutical dosage forms such as tablets or granules, a process for recrystallizing or purifying a chemical compound such as a pharmaceutically active compound, etc.

A relevant parameter of the process for preparing a sample is any parameter or condition which will have an influence on the outcome of the process. Examples are the amounts and ratios of starting compounds or intermediates used in a chemical reaction, the type and amount of solvents used in such reaction, pressure, temperature, the use of an inert gas atmosphere, the time period of using a chemical or physical operation such as recrystallization, reslurrying, washing etc.

Metadata means descriptive data or, in other words, "data about other data". Metadata provides information about, or documentation of, other data obtained from an application such as an analytical experiment. Thus, it can be used to designate or define the structure of the primary data. Metadata may include descriptive information about the context, quality and condition or characteristics of the primary data.

An analytical report is a document or set of data containing metadata and primary data based on the results of an analytical experiment and being stored on a computer or another suitable device for the electronic storage of data.

A correlation matrix is a matrix including at least two sets of data characterized at least by i) sample name, ii) method code (Hash value), iii) name of the experiment and iv) relevant results obtained in the experiment. It contains data resulting from the use of at least two different analytical experiments each experiment characterized by a unique analytical method code. If the matrix consists of one table only, e.g. an Excel table, it may also be called correlation table. A multitude of tables may be combined into a correlation matrix.

Multivariate analysis means applying a statistical analysis based on the statistical principle of multivariate statistics, which involves observation and analysis of more than one statistical variable at a time.

The advantages of the present invention are obtained by using a so-called Hash value (unique analytical method code) for describing a specific analytical method and the specific parameters and conditions used (which parameters and conditions will have an effect on the results of the analytical experiment using said method and parameters/conditions). Thereby, a large number of samples measured using the same Hash value can be easily or ganized.

Also, the process of the present invention uses a reference sample as defined hereinabove. Using the combination of Hash value and reference sample, it is possible to automatically organize and compare different samples within the same and, significantly, between different Hash value groups.

The process of the invention therefore enables one to use automatic extraction templates (for automatic data extraction, calculation and sorting of data from analytical reports, for example by using a Waters SDMS extraction template (SDMS=scientific data management system). The template is used on the sets of data resulting from step (v) of the process of the invention. The so organized data can then be processed into a correlation matrix or table for further analysis.

The correlation between the groups/plurality of samples characterized by different Hash values can be done by using the reference sample (e.g. a crude product of a chemical synthesis with all known and unknown relevant impurities which crude product is measured every time the method is changed and a new Hash value generated).

For example, in case of HPLC used as the analytical method, this approach allows one to easily compare the relative retention times obtained in different experiments. For example, by using the process of the present invention a large amount of data can be processed into a correlation matrix, e.g. data obtained from 1000 chromatograms, including Hash value, sample names and the peaks of the chromatograms, in an automatic and fast manner (e.g. within seconds or minutes) as compared to the conventional (manual) approach which may take days and weeks. Thus, the data organization and analysis process is accelerated by a factor of e.g. 100, 1000 or even more, depending to some extent on the power of the processor and data storage system used in this approach.

The process of the present invention is applicable to any analytical method where the results are numerical or can be transferred into a numerical format and wherein the results depend on the "input" parameters/conditions of the analytical method.

As stated above, the process of the present invention generally starts with selecting an analytical method for use in an analytical experiment such as chromatography, in particular high throughput liquid chromatography (HPLC) (step (i)). The step of selecting a method may involve modifications to be made to known analytical methods or even include the creation of a new analytical method.

Other examples of suitable analytical methods are gas chromatography (GC), supercritical fluid chromatography (SFC), thin layer chromatography (TLC), electrophoresis, etc. . . . .

Then, the relevant working parameters and conditions of the selected method are determined (step (ii)), such as temperature or type and composition of an HPLC column, composition of HPLC mobile phase, etc., which parameters and conditions have an effect on the results obtained by using the selected method.

In a further step of the process of the present invention, a unique analytical method code (Hash value) is assigned to a set of data, said set of data including a) the type of the selected method and b) a specific combination of the working parameters and conditions used in the analytical experiment (step (iii)). Specific sets of data are illustrated in the examples of the present specification.

In a further step of the process of the present invention (step (iv)), the method characterized by said Hash value is applied to at least one reference sample and at least one or more further samples obtained from a process for preparing said samples, such as a chemical, pharmaceutical, physical or biochemical process such as in particular a process for synthesizing or purifying a chemical compound, in which process at least one parameter such as temperature, solvent, or ratio of reactants etc. is to be optimized.

For example, the process may be one for synthesizing a pharmaceutically active substance or for preparing specific forms of pharmaceutically active substances such as hydrates, polymorphs, salts or other derivatives.

The nature of the reference sample(s) is as explained hereinabove. Furthermore, it is noted that the reference sample can be one or more samples adequately stored in conditions where degradation is substantially absent or at least very limited. If this is not possible, the standard route of synthesis/purification/etc. for a specific reference sample is used every time when this sample is needed to obtain an HPLC or other type of chromatogram with the 'standard' impurity profile, i.e. showing all impurities or other relevant components which will appear in this reaction.

In a further step of the process of the present invention (step (v)), the Hash value and the name of the sample are stored as metadata together with the analytical results obtained in step (iv) as an analytical report.

The analytical results obtained in step (iv) are usually based on or consist of a plurality of response signals such as an assay of peaks having different retention times obtained in HPLC. One or more response signals are also referred to as "the measured data".

In a further step of the process of the present invention (step (vi)), the relevant metadata and if required further data from the analytical reports (Hash value, sample name, etc.) are automatically extracted, e.g. by using an extraction template or another extraction process, and transferred to an enterprise content management system (ECMS) or other database system.

In a further step of the process of the present invention (step (vii)), the results are "automatically organized" according to the Hash value in the ECMS or any other suitable database systems. In this context, it is noted that automatically organized means that there is a script or extraction template (computer assisted procedure) which, while storing the data to ECM system, has the function that the metadata and predefined data from the report are automatically parsed/extracted/taken-out to the ECM system or database. Thus, in accordance with the invention, sample name, analytical method code name, RRTs and amounts/area % and other data or metadata are parsed automatically.

In a further step of the process of the present invention (step (viii)), the sets of data characterized by different Hash values are correlated on the basis of the reference sample measured for each Hash value, thereby creating a correlation matrix or table.

In this respect, it is noted that for reference samples a correlation between the measured data (e.g. the RRT of an HPLC peak) and the attribute of interest (e.g. the chemical structure of the impurity which is characterized by the measured RRT) is to be established. In this respect, standard procedures like HPLC-MS, HPLC-MS/MS, HPLC-NMR technique or isolation (using HPLC-preparative methods or MPLC-preparative method) or synthesis of the relevant impurity are used.

As long as there is no defined structure for a certain peak, the label of the peak should be based on a combination of its RRT and the analytical method code used in the experiment. See, for example, Table 2b hereinbelow where Impurity 1 is characterized by RRT 0.224 and Analytical Method Code LC0001-00 (according to the first analytical method) and is later found to be equal to RRT 0.300 measured with the second analytical method assigned Method Code LC0001-01.

If RRTs for a specific impurity are identified in all analytical methods, the label of said impurity (like RRT 0.224_LC0001-00) could be assigned another name like PALCA (see Table 2b) which is then used for this identified impurity in further experiments and analyses.

If RRTs for a specific impurity are not identified in all analytical methods, the label stays like it is (like RRT 0.224_LC0001-00) and such impurity should not be used for DoE (=Design of Experiment) optimization.

Thus, in general, only if the RRT for a specific impurity is determined by all used analytical methods, said impurity is included in the following multivariate analyses.

Furthermore, based on the type of optimization, e.g. reaction screening or optimization, purification screening or optimization, a pre-determined limit may be set on the data used for multivariate analyses. For example, only those peaks of a chromatogram may be used which show a minimum intensity. For example, more than 1% or 2% for reaction screening and more than 0.5% for reaction optimization or more than 0.1% for final purification screening or more than 0.05% for final purification optimization. In general, the specific limit chosen will depend on the type of process and/or degree of optimization desired by the chemist. In other words, in the development of a purification process the limit set for the minimum intensity of a peak may differ from the limit set for this data in the context of a screening process, i.e. a process testing a large number of reaction conditions for a specific route of synthesis.

For HPLC as the analytical method, the above limits can be defined in terms of area % or wt % (ppm) of the chromatogram measured.

In a further step of the process of the present invention (step (ix)), the correlation matrix including the data as described above, e.g. data based on HPLC peaks characterized by a pre-determined minimum intensity, is used for multivariate analysis of the one or more of the parameters of the process resulting in the samples recited in step (iv) of the process as defined hereinabove.

In a further step of the process of the present invention, the results of the multivariate analysis are optionally visualized as one or more graphic charts.

In a further step of the process of the present invention, the results of steps (ix) and, optionally, step (x) as defined hereinabove, are used to optimize said one or more parameters of the process as defined in step (iv).

Optionally, in a further step of the process of the present invention, the optimized process is verified on the laboratory, pilot plant or industrial scale.

In a preferred embodiment of the invention, the present invention provides a process for the automated classification and analysis of raw data obtained by chromatography, in particular high pressure liquid chromatography (HPLC), said process comprising the following steps:

i) selecting chromatography, in particular high pressure liquid chromatography (HPLC), as the analytical method for use in an analytical experiment;

ii) determining working parameters and conditions for the selected method, such as temperature or type and composition of an HPLC column, composition of an HPLC mobile phase, etc., which parameters and conditions have an effect on the results obtained by using the selected method;

iii) assigning to a set of data, said set of data including a) the type of the selected method and b) a specific combination of working parameters and conditions used in the analytical experiment, a unique analytical method code (Hash value);

iv) applying the method characterized by said Hash value to at least one reference sample and at least one or more further samples obtained from a process for preparing said samples, said process being a process for synthesizing or purifying a chemical compound, in which process at least one parameter such as temperature, solvent, or ratio of reactants etc. is to be optimized;

v) storing the Hash value and the name of the sample as metadata together with the analytical results obtained in step (iv) as an analytical report;

vi) automatically extracting, e.g. by using an extraction template or another extraction process, the relevant metadata from the analytical reports (Hash value, sample name, etc.) and transferring them to an enterprise content management system (ECMS) or other database systems;

vii) automatically organizing the results according to the Hash value in the ECMS or any other suitable database system;

viii) correlating the sets of data characterized by different Hash values on the basis of the reference sample measured for each Hash value, thereby creating a correlation matrix or table;

ix) using the correlation matrix or table for multivariate analysis of the one or more of the parameters of the process resulting in the samples recited in step (iv);

x) optionally, visualizing the results as one or more graphic charts;

xi) using the results of steps (ix) and, optionally, step (x) to optimize said one or more parameters of the process as defined in step (iv);

xii) optionally, verifying the process on the laboratory, pilot plant or industrial scale.

As discussed in detail hereinabove, the present invention provides a process which allows for the above type of analysis in a more efficient manner as in the prior art. This is because of the following advantages offered by the present invention, which are explained for illustration in the context of HPLC as the analytical method.

First, using an arrangement of data in accordance with the present invention, which arrangement is characterized by clustering of data (according to the unique analytical method codes) and use of analyses of reference samples with all the methods characterized by a unique analytical method code, it is possible to obtain a systematic, automatic and fast link between the specific HPLC peaks (specific RRTs) and the impurities related to those peaks on a whole set of samples.

Second, the possibility of setting critical HPLC parameters such as minimum intensities ensures that only those RRTs (impurities) are used which are inside an allowed window. Thereby, a 'mix-up' in the correlation process is avoided and there is sufficient confidence in the results obtained by the subsequent multivariate analysis.

The results of the process of the present invention can be used beneficially in the design of experiments (DoE).

The following examples illustrate the present invention.

EXAMPLES

The method of the present invention was used to optimize the molar ratio and the solvent system of a two-component chemical reaction resulting in the formation of a pharmaceutically active chemical compound. Specifically, 6-fluoro-3-(4-piperidinyl)-1,2-benzisoxazole hydrochloride (Compound I) and 3-(2-chloroethyl-9-hydroxy-2-methyl-6,7,8,9-tetrahydro-4H-pyrido{1,2-a]pyrimidin-4-one (Compound 2) were reacted in a solvent system based on methanol, an organic base and 2-propanol to result in 3-(2-(4-(6-fluorobenzo[d]isocazol-3-yl)piperidin-1-yl)ethyl-9-hydroxy-2-methyl-6,7,8,9-tetrahydro-4H-pyrido{1,2-a]pyrimidin-4-one (Compound 3). The route of synthesis is shown in Scheme 1 below.

6-fluoro-3-(4-piperidinyl)-1,2-benzisoxazole hydrochloride
PAL41

3-(2-chloroethyl)-9-hydroxy-2-methyl-6,7,8,9-tetrahydro-4H-pyrido[1,2-a]pyrimidin-4-one
PAL72

ROS1
1. Methanol/organic base
2. 2-propanol 3-(2-(4-(6-fluorobenzo[d]isoxazol-3-yl)piperidin-1-yl)ethyl)-9-hydroxy-2-methyl-6,7,8,9-tetrahydro-4H-pyrido[1,2-a]pyrimidin-4-one
PALCA Example 1

A reference sample, i.e. a sample based on the reaction mixture which contains both the starting compounds and the (crude) reaction product was analyzed in a HPLC experiment. The relevant parameters of the HPLC experiment are set out below. This set of parameters/conditions characterizing the method used was assigned method code LC 0001-00. The reference sample was assigned the name PALCA-1135/3OB.

Column: Gemini NX C18, 150×4.6 mm, 3 μm particles,
Mobile phase: solvent A: 0.01 M $NaH_2PO_4*H_2O$ pH=4.0; solvent B: ACN:MeOH=30:70
Gradient elution:

| Time (min) | Solvent A (%) | Solvent B (%) |
|---|---|---|
| 0 | 85 | 15 |
| 18 | 68 | 32 |
| 27 | 10 | 90 |
| 30 | 10 | 90 |
| 31 | 85 | 15 |

Post run=3 minutes
Detection=UV, wavelength 238 nm,
Flow rate=1.0 ml/min,
Injection volume=5 μl,
Column temperature=35° C.

Dilution solvent=mixture of buffer (0.01M NaH2PO4 pH=4.0) and acetonitrile in the ratio 1:1

Figure 1:
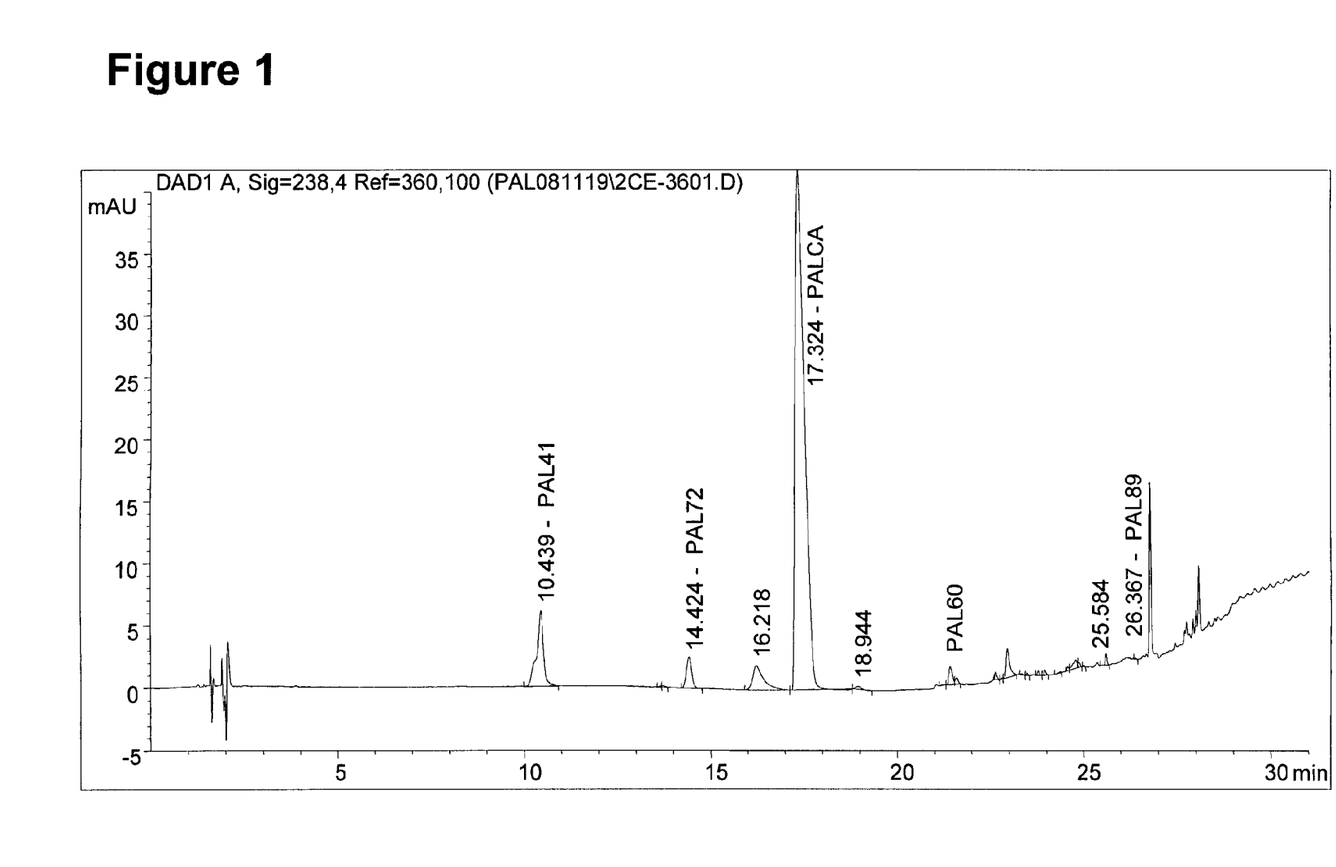
FIG. 1 shows a chromatogram obtained during an analytical experiment described in Example 1.

The details of the chromatogram are shown in FIG. 1.

Example 2

Reference sample PALCA-1135/3OB from Example 1 was analyzed in a further HPLC experiment characterized by a second set of parameters/conditions. The parameters of the experiment are set out below. The set of parameters/conditions characterizing the method used in this example was assigned method code LC 0001-01.

Figure 2:
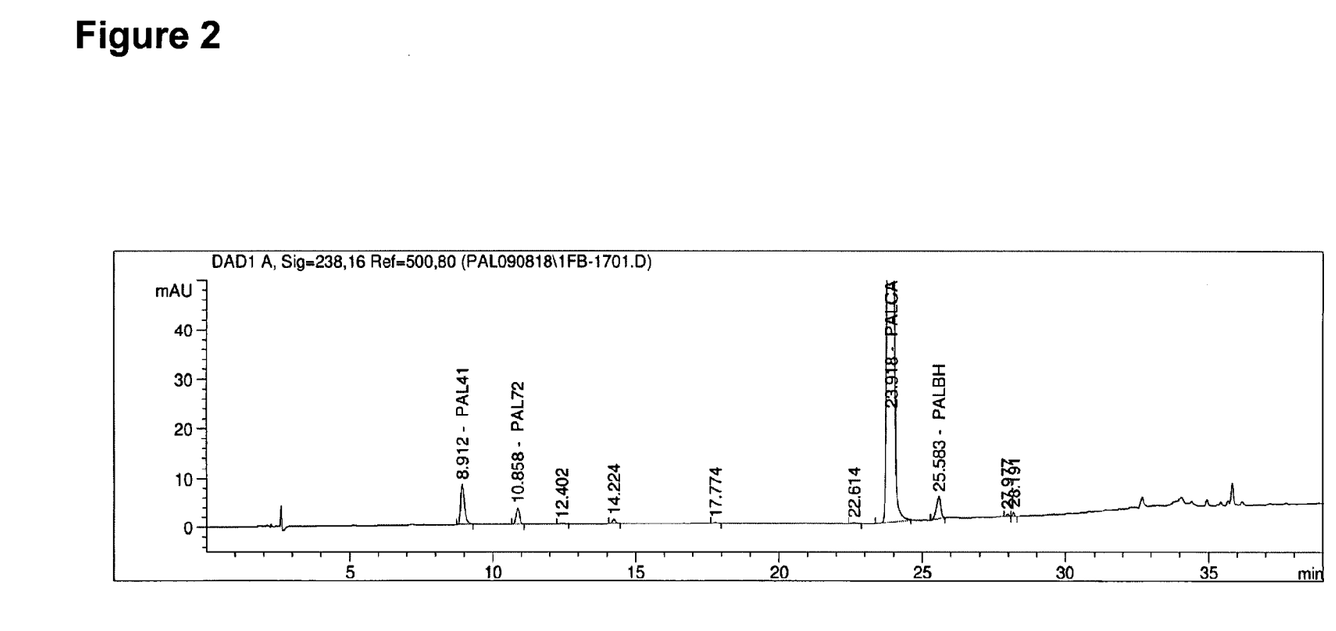
FIG. 2 shows a chromatogram obtained during the analytical experiment described in Example 2.
Figure 3:
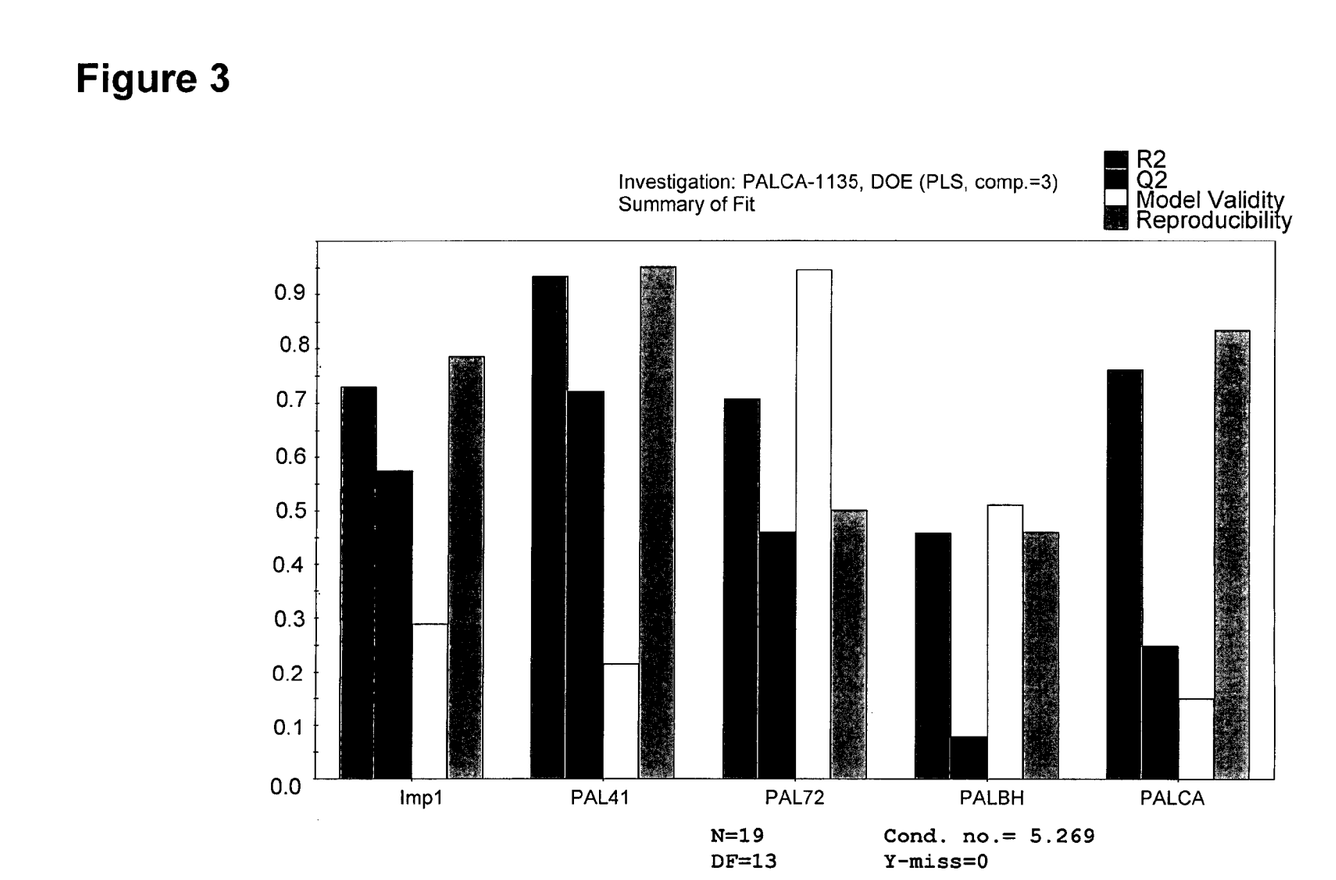
FIG. 3 shows a so-called Summary of Fit which provides information about the quality of the model used to calculate the fit. For example, if $R^2$ (=fraction of the variation of the response explained by the model), $Q^2$ (=fraction of the variation of the response predicted by the model according to cross validation), model validity and reproducibility are high, the model is considered to be solid and valid.
Figure 4:
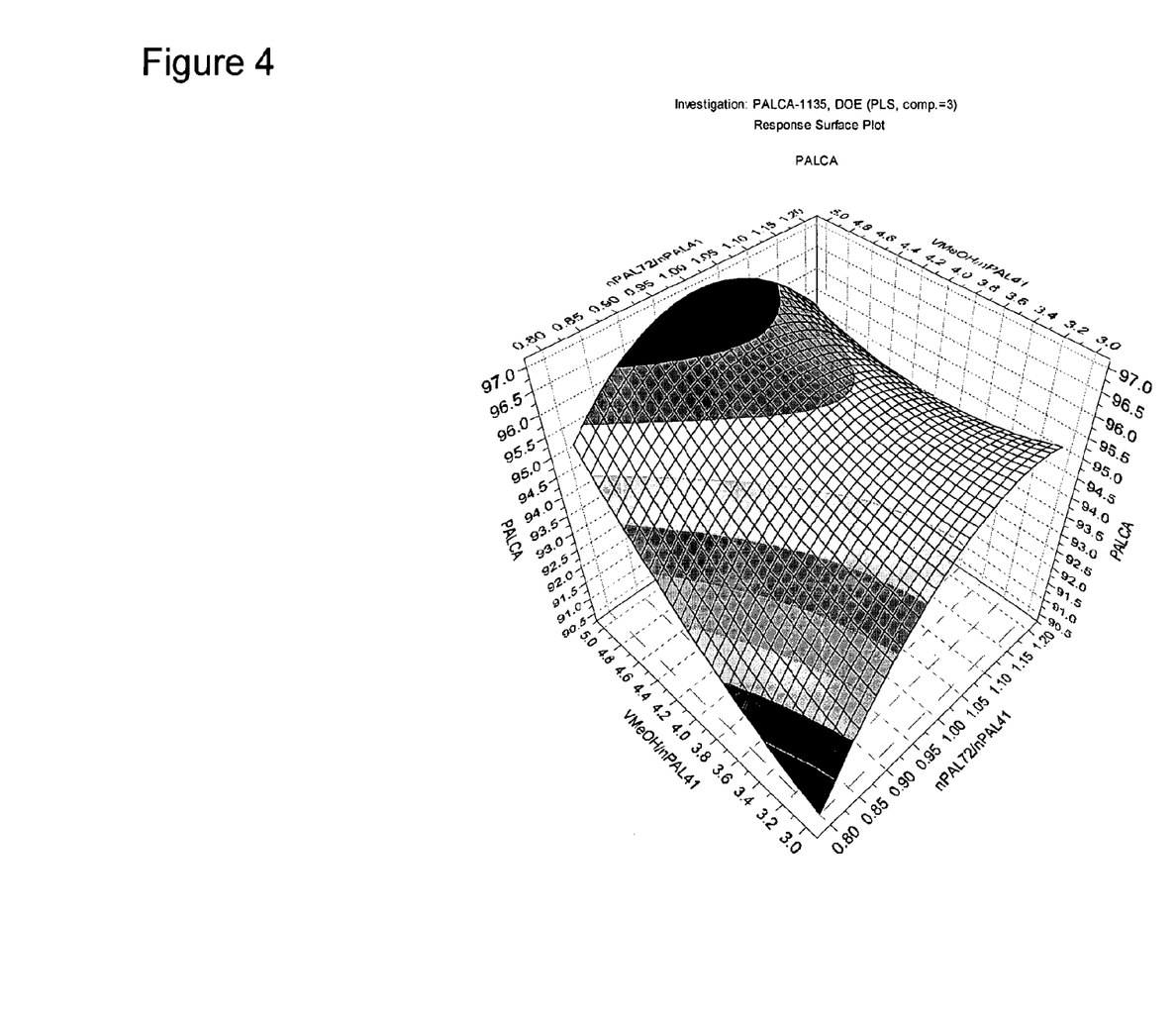
FIG. 4 shows a response surface plot for the main product termed PALCA in Scheme 1.
Figure 5:
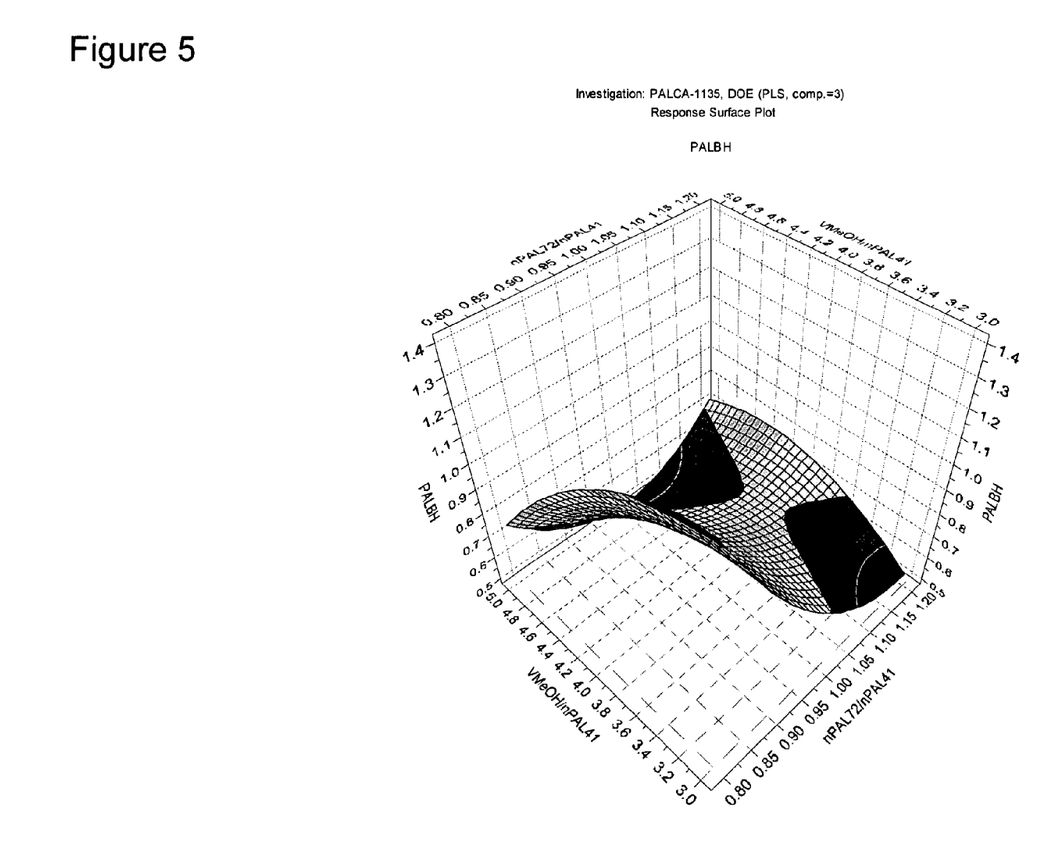
FIG. 5 shows a response surface plot for the impurity termed PALBH in Scheme 1.
Figure 6:
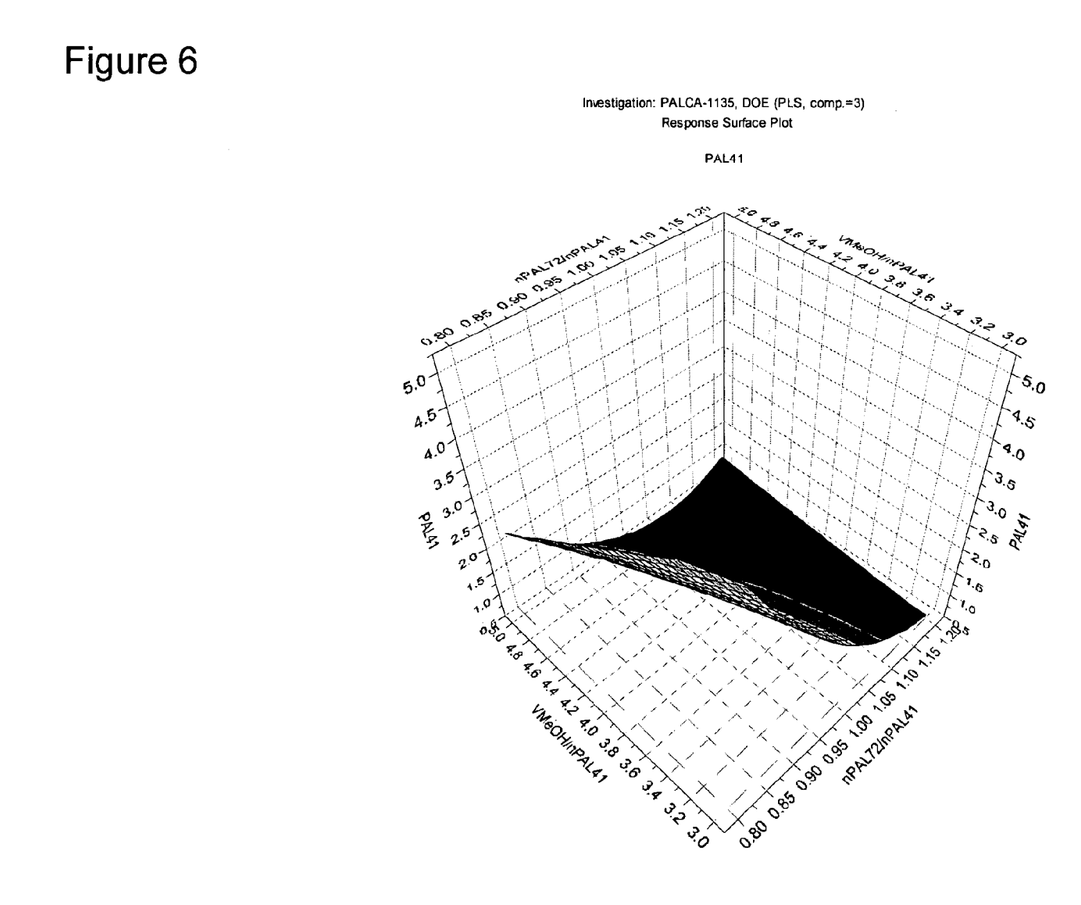
FIG. 6 shows a response surface plot for the starting intermediate termed PAL41 in Scheme 1.
Figure 7:
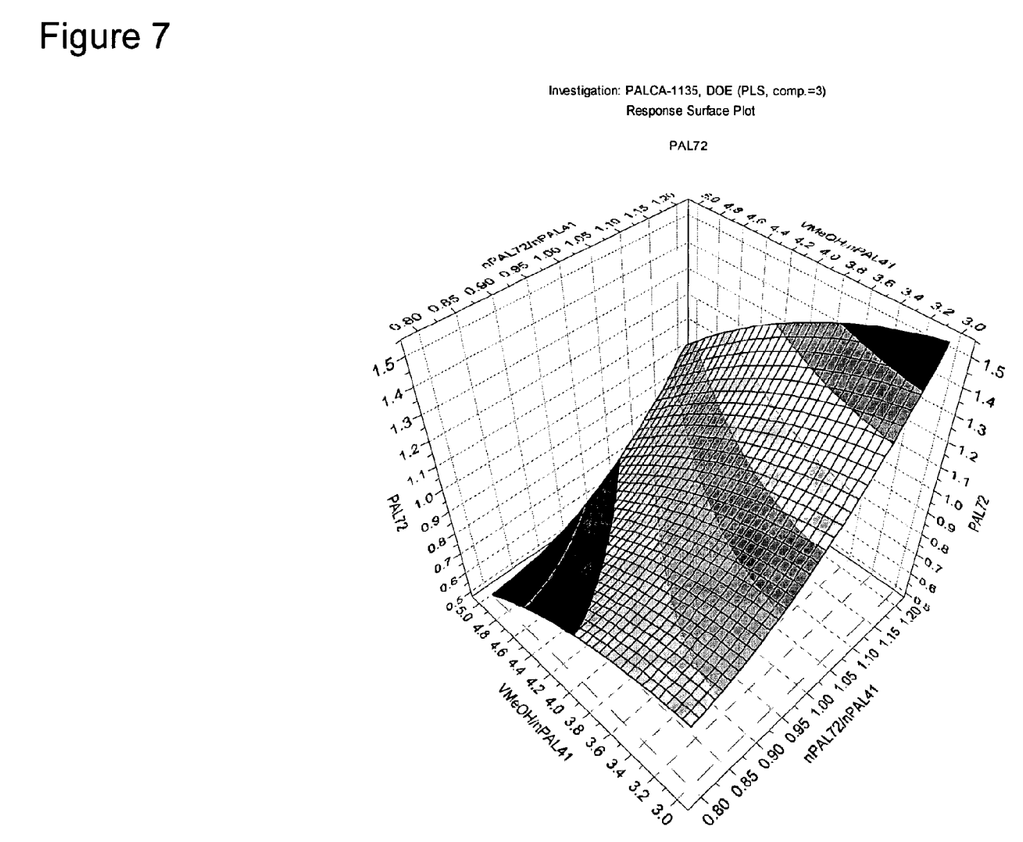
FIG. 7 shows a response surface plot for the starting intermediate termed PAL72 in Scheme 1.

The details of the chromatogram are shown in FIG. 2.

Column: Gemini NX C18, 150×4.6 mm, 3 μm particles,

Mobile phase: solvent A: 0.01 M $NaH_2PO_4*H_2O$ pH=6.5; solvent B: ACN; solvent C: MeOH Gradient elution:

| Time (min) | Solvent A (%) | Solvent B (%) | Solvent C (%) |
|---|---|---|---|
| 0 | 80 | 14 | 6 |
| 5 | 80 | 14 | 6 |
| 20 | 65 | 24.5 | 10.5 |
| 30 | 10 | 56 | 24 |
| 38 | 90 | 63 | 27 |
| 39 | 80 | 14 | 6 |

Post run=4 minutes
Detection=UV, wavelength 238 nm,
Flow rate=0.7 ml/min,
Injection volume=5 μl,
Column temperature=35° C.
Dilution solvent=mixture of buffer (0.01M NaH2PO4 pH=4.0) and acetonitrile in the ratio 1:1

Example 3

In a further series of experiments, the analytical methods characterized by the above method codes LC0001-00 and LC0001-01 were applied to further samples obtained when conducting the chemical synthesis resulting in Compound 3 and varying relevant parameters of the chemical synthesis. Specifically, the molar ratio of Compound 1 to Compound 2 and the volume of the reaction solvent methanol were varied. The results are shown in Tables 1a and 1b which include the peaks obtained in the HPLC analysis. In both tables, only the first of the plurality of peaks are shown (relative retention times (RRTs) 0.149 to 0.444 in Table 1a and RRTs from 0.133 to 0.316 in Table 1b).

TABLE 1a

| Exp No | Exp Name | Run order | Incl/Excl | nPAL72/nPAL41 | VMeOH/n PAL41 | Analytical Method Code | Impurity label RRT | RRT 0.149 LC0001-00 0.149 | RRT 0.194 LC0001-00 0.194 | RRT 0.196 LC0001-00 0.196 | Imp1 0.224 | RRT 0.444 LC0001-00 0.444 |
|---|---|---|---|---|---|---|---|---|---|---|---|---|
| 2 | PALCA-1135/2 | 9 | Incl | 1.2 | 3 | LC0001-00 | | 0.00 | 0.04 | 0.11 | 0.19 | 0.00 |
| 3 | PALCA-1135/3 | 5 | Incl | 0.8 | 5 | LC0001-00 | | 0.00 | 0.00 | 0.00 | 0.00 | 0.00 |
| 4 | PALCA-1135/4 | 4 | Incl | 1.2 | 5 | LC0001-00 | | 0.00 | 0.00 | 0.09 | 0.11 | 0.00 |
| 5 | PALCA-1135/5 | 11 | Incl | 0.8 | 4 | LC0001-00 | | 0.00 | 0.00 | 0.00 | 0.02 | 0.00 |
| 6 | PALCA-1135/6 | 7 | Incl | 1.2 | 4 | LC0001-00 | | 0.00 | 0.02 | 0.04 | 0.07 | 0.00 |
| 8 | PALCA-1135/8 | 3 | Incl | 1 | 5 | LC0001-00 | | 0.00 | 0.00 | 0.00 | 0.03 | 0.00 |
| 10 | PALCA-1135/10 | 6 | Incl | 1 | 4 | LC0001-00 | | 0.03 | 0.00 | 0.00 | 0.04 | 0.00 |
| 11 | PALCA-1135/11 | 8 | Incl | 1 | 4 | LC0001-00 | | 0.01 | 0.00 | 0.00 | 0.02 | 0.00 |
| 13 | PALCA-1139 | 13 | Incl | 1.05 | 5 | LC0001-00 | | 0.00 | 0.00 | 0.00 | 0.00 | 0.00 |
| 14 | PALCA-1141 | 14 | Incl | 1.05 | 5 | LC0001-00 | | 0.00 | 0.00 | 0.00 | 0.00 | 0.00 |
| 15 | PALCA-1148 | 15 | Incl | 1.05 | 5 | LC0001-00 | | 0.00 | 0.00 | 0.00 | 0.00 | 0.00 |
| 16 | PALCA-1165 | 16 | Incl | 1.05 | 5 | LC0001-00 | | 0.00 | 0.00 | 0.00 | 0.00 | 0.00 |
| 17 | PALCA-1166 | 17 | Incl | 1.05 | 5 | LC0001-00 | | 0.00 | 0.00 | 0.00 | 0.00 | 0.00 |
| 18 | PALCA-1179 | 18 | Incl | 1.05 | 5 | LC0001-00 | | 0.00 | 0.00 | 0.00 | 0.00 | 0.00 |
| 19 | PALCA-1184 | 19 | Incl | 1.05 | 5 | LC0001-00 | | 0.00 | 0.00 | 0.00 | 0.00 | 0.00 |

TABLE 1b

| Exp No | Exp Name | Run order | Incl/Excl | nPAL72/nPAL41 | VMeOH/n PAL41 | Analytical Method Code | Impurity label RRT | RRT 0.133 LC0001-01 0.133 | RRT 0.215 LC0001-01 0.215 | RRT 0.280 LC0001-01 0.280 | Imp1 0.300 | RRT 0.316 LC0001-01 0.316 |
|---|---|---|---|---|---|---|---|---|---|---|---|---|
| 1 | PALCA-1135/1 | 1 | Incl | 0.8 | 3 | LC0001-01 | | 0.00 | 0.00 | 0.00 | 0.05 | 0.00 |
| 3 | PALCA-1135/3 | 5 | Incl | 0.8 | 5 | LC0001-01 | | 0.00 | 0.00 | 0.00 | 0.00 | 0.00 |
| 7 | PALCA-1135/7 | 2 | Incl | 1 | 3 | LC0001-01 | | 0.00 | 0.11 | 0.00 | 0.15 | 0.15 |
| 9 | PALCA-1135/9 | 10 | Incl | 1 | 4 | LC0001-01 | | 0.00 | 0.07 | 0.00 | 0.11 | 0.12 |
| 12 | PALCA-1135/13 | 12 | Incl | 1.2 | 3 | LC0001-01 | | 0.09 | 0.36 | 0.00 | 0.12 | 0.04 |

Tables 2a and 2b show the HPLC peaks obtained in the above-described experiments after elimination of those peaks having a peak area in % of less than 0.50%, based on the total peak area of the chromatogram, and unidentified/uncorrelated peaks between both methods.

TABLE 2a

| | | | | | | | Peak Identification | | | | |
|---|---|---|---|---|---|---|---|---|---|---|---|
| Exp No | Exp Name | Run order | Incl/ Excl | nPAL/ nPAL41 | VMeOH/ nPAL41 | Analytical Method Code | Impurity label RRT | Imp1 RRT 0.224 LC0001-00 = RRT 0.300 LC0001-01 0.224 | PAL41 RRT 0.601 LC0001-00 0.601 | PAL72 RRT 0.833 LC0001-00 0.833 | PALBH RRT 0.936 LC0001-00 0.936 | PALCA RRT 1.000 LC0001-00 1.000 |
| 2 | PALCA-1135/2 | 9 | Incl | 1.2 | 3 | LC0001-00 | | 0.19 | 0.71 | 1.70 | 0.52 | 95.16 |
| 3 | PALCA-1135/3 | 5 | Incl | 0.8 | 5 | LC0001-00 | | 0.00 | 2.08 | 0.64 | 1.03 | 94.87 |
| 4 | PALCA-1135/4 | 4 | Incl | 1.2 | 5 | LC0001-00 | | 0.11 | 0.55 | 1.26 | 0.94 | 94.70 |
| 5 | PALCA-1135/5 | 11 | Incl | 0.8 | 4 | LC0001-00 | | 0.02 | 3.70 | 0.65 | 1.12 | 92.37 |
| 6 | PALCA-1135/6 | 7 | Incl | 1.2 | 4 | LC0001-00 | | 0.07 | 0.72 | 1.42 | 0.73 | 95.30 |
| 8 | PALCA-1135/8 | 3 | Incl | 1 | 5 | LC0001-00 | | 0.03 | 1.56 | 0.63 | 0.66 | 95.42 |
| 10 | PALCA-1135/10 | 6 | Incl | 1 | 4 | LC0001-00 | | 0.04 | 2.01 | 0.89 | 0.44 | 94.52 |
| 11 | PALCA-1135/11 | 8 | Incl | 1 | 4 | LC0001-00 | | 0.02 | 1.03 | 0.86 | 1.03 | 95.19 |
| 13 | PALCA-1139 | 13 | Incl | 1.05 | 5 | LC0001-00 | | 0.00 | 0.59 | 0.90 | 0.48 | 96.43 |
| 14 | PALCA-1141 | 14 | Incl | 1.05 | 5 | LC0001-00 | | 0.00 | 0.55 | 0.82 | 0.67 | 96.69 |
| 15 | PALCA-1148 | 15 | Incl | 1.05 | 5 | LC0001-00 | | 0.00 | 0.25 | 0.49 | 0.15 | 98.52 |
| 16 | PALCA-1165 | 16 | Incl | 1.05 | 5 | LC0001-00 | | 0.00 | 0.28 | 0.73 | 0.16 | 98.44 |
| 17 | PALCA-1166 | 17 | Incl | 1.05 | 5 | LC0001-00 | | 0.00 | 0.26 | 0.08 | 0.22 | 98.43 |
| 18 | PALCA-1179 | 18 | Incl | 1.05 | 5 | LC0001-00 | | 0.00 | 0.59 | 0.86 | 0.67 | 96.78 |
| 19 | PALCA-1184 | 19 | Incl | 1.05 | 5 | LC0001-00 | | 0.00 | 0.57 | 0.90 | 0.34 | 97.63 |

TABLE 2b

| | | | | | | | | Peak Identification | | | | |
|---|---|---|---|---|---|---|---|---|---|---|---|---|
| Exp No | Exp Name | Run order | Incl/ Excl | nPAL/ nPAL41 | VMeOH/ nPAL41 | Analytical Method Code | Impurity label RRT | Imp1 RRT 0.224 LC0001-00 = RRT 0.300 LC0001-01 0.300 | PAL41 RRT 0.370 LC0001-00 0.370 | PAL72 RRT 0.450 LC0001-00 0.450 | PALCA 1.000 | PALBH 1.070 |
| 1 | PALCA-1135/1 | 1 | Incl | 0.8 | 3 | LC0001-01 | | 0.05 | 5.17 | 0.83 | 91.22 | 1.14 |
| 3 | PALCA-1135/3 | 5 | Incl | 0.8 | 5 | LC0001-01 | | 0.00 | 1.85 | 0.66 | 95.85 | 1.10 |
| 7 | PALCA-1135/7 | 2 | Incl | 1 | 3 | LC0001-01 | | 0.15 | 1.80 | 0.96 | 92.69 | 1.21 |
| 9 | PALCA-1135/9 | 10 | Incl | 1 | 4 | LC0001-01 | | 0.11 | 1.28 | 0.82 | 94.13 | 1.21 |
| 12 | PALCA-1135/13 | 12 | Incl | 1.2 | 3 | LC0001-01 | | 0.12 | 0.51 | 1.40 | 96.24 | 0.32 |

Table 3 contains the relevant data from both series of experiments as stated in Tables 1a/1b and 2a/2b. The capability to include those data in one table (correlation matrix/table for further data analysis results from the use of the combination of reference sample and method codes (Hash values). The data in Table 3 were then used for the application of multivariate analysis.

TABLE 3

| Exp No | Exp Name | Run order | Incl/ Excl | nPAL72/ nPAL41 | VMeOH/ n PAL41 | Analytical Method Codes LC0001-00 and LC0001-01 Imp1 RRT 0.224 LC0001 PAL41 | RRT 0 PAL72 | RRT 0.833 LC0001-00 | PALBH RRT 0.936 LC0001-00 | PALCA RRT 1.000 LC0001-00 |
|---|---|---|---|---|---|---|---|---|---|---|
| 2 | PALCA-1135/2 | 9 | Incl | 1.2 | 3 | 0.19 | 0.71 | 1.70 | 0.52 | 95.16 |
| 3 | PALCA-1135/3 | 5 | Incl | 0.8 | 5 | 0.00 | 2.08 | 0.64 | 1.03 | 94.87 |

TABLE 3-continued

| Exp No | Analytical Method Codes LC0001-00 and LC0001-01 Exp Name | Run order | Incl/ Excl | nPAL72/ nPAL41 | VMeOH/ n PAL41 | Imp1 RRT 0.224 LC0001 PAL41 | RRT 0 PAL72 | RRT 0.833 LC0001-00 | PALBH RRT 0.936 LC0001-00 | PALCA RRT 1.000 LC0001-00 |
|---|---|---|---|---|---|---|---|---|---|---|
| 4  | PALCA-1135/4  | 4  | Incl | 1.2  | 5 | 0.11 | 0.55 | 1.26 | 0.94 | 94.70 |
| 5  | PALCA-1135/5  | 11 | Incl | 0.8  | 4 | 0.02 | 3.70 | 0.65 | 1.12 | 92.37 |
| 6  | PALCA-1135/6  | 7  | Incl | 1.2  | 4 | 0.07 | 0.72 | 1.42 | 0.73 | 95.30 |
| 8  | PALCA-1135/8  | 3  | Incl | 1    | 5 | 0.03 | 1.56 | 0.63 | 0.66 | 95.42 |
| 10 | PALCA-1135/10 | 6  | Incl | 1    | 4 | 0.04 | 2.01 | 0.89 | 0.44 | 94.52 |
| 11 | PALCA-1135/11 | 8  | Incl | 1    | 4 | 0.02 | 1.03 | 0.86 | 1.03 | 95.19 |
| 13 | PALCA-1139    | 13 | Incl | 1.05 | 5 | 0.00 | 0.59 | 0.90 | 0.48 | 96.43 |
| 14 | PALCA-1141    | 14 | Incl | 1.05 | 5 | 0.00 | 0.55 | 0.82 | 0.67 | 96.69 |
| 15 | PALCA-1148    | 15 | Incl | 1.05 | 5 | 0.00 | 0.25 | 0.49 | 0.15 | 98.52 |
| 16 | PALCA-1165    | 16 | Incl | 1.05 | 5 | 0.00 | 0.28 | 0.73 | 0.16 | 98.44 |
| 17 | PALCA-1166    | 17 | Incl | 1.05 | 5 | 0.00 | 0.26 | 0.08 | 0.22 | 98.43 |
| 18 | PALCA-1179    | 18 | Incl | 1.05 | 5 | 0.00 | 0.59 | 0.86 | 0.67 | 96.78 |
| 19 | PALCA-1184    | 19 | Incl | 1.05 | 5 | 0.00 | 0.57 | 0.90 | 0.34 | 97.63 |
| 1  | PALCA-1135/1  | 1  | Incl | 0.8  | 3 | 0.05 | 5.17 | 0.83 | 1.14 | 91.22 |
| 3  | PALCA-1135/3  | 5  | Incl | 0.8  | 5 | 0.00 | 1.85 | 0.66 | 1.10 | 95.85 |
| 7  | PALCA-1135/7  | 2  | Incl | 1    | 3 | 0.15 | 1.80 | 0.96 | 1.21 | 92.69 |
| 9  | PALCA-1135/9  | 10 | Incl | 1    | 4 | 0.11 | 1.28 | 0.82 | 1.21 | 94.13 |
| 12 | PALCA-1135/13 | 12 | Incl | 1.2  | 3 | 0.12 | 0.51 | 1.40 | 0.32 | 96.24 |

FIGS. 3 to 7 are graphic representations of the results of the multivariate analyses run on the data summarized in Table 3.

The invention claimed is:

1. A process for optimizing one or more parameters of a process for synthesizing or purifying a chemical compound comprising the automated classification and analysis of data, in which process at least one synthesis or purification process parameter is to be optimized, said process comprising the following steps:
  i) selecting an analytical method selected from the group consisting of chromatography, high pressure liquid chromatography (HPLC), gas chromatography (GC), super-critical fluid chromatography (SFC), and thin layer chromatography (TLC) for use in an analytical experiment;
  ii) determining working parameters and conditions for the selected method, which parameters and conditions have an effect on results obtained by using the selected method;
  iii) assigning to a set of data a unique analytical method code (Hash value),
     said set of data including a) the selected method and b) a specific combination of working parameters and conditions used in the analytical experiment,
     said set of data being of a predetermined limit based on a minimum intensity of 0.05% of a chromatographic peak obtained when using chromatography as the analytical method of step (i);
  iv) conducting the process for synthesizing or purifying said chemical compound to obtain at least one reference sample and at least one or more further samples, in which process the one or more parameters are to be optimized, and conducting the analytical method characterized by said Hash value for the at least one reference sample and the at least one or more further samples;
  v) storing the Hash value and the name of the sample as metadata together with the analytical results obtained in step (iv) as an analytical report;
  vi) automatically extracting by using an extraction template or another extraction process the metadata and further data from the analytical reports and transferring them to an enterprise content management system (ECMS) or other database systems;
  vii) automatically organizing by means of a computer-assisted procedure the results according to the Hash value in the ECMS or any other suitable database system,
  viii) correlating the sets of data characterized by different Hash values on the basis of the reference sample measured for each Hash value, thereby creating a correlation matrix/table;
  ix) using the correlation matrix/table for multivariate analysis of the one or more of the synthesis or purification process parameters resulting in the samples recited in step (iv),
  x) wherein said one or more synthesis or purification process parameters as defined in step (iv) are optimized by using the results of step (ix); and
  xi) synthesizing or purifying the chemical compound using the process and the one or more parameters which have been optimized.

2. Process according to claim 1, wherein after step (ix) the results as visualized as one or more graphic charts.

3. Process according to claim 1, wherein the process is verified on the laboratory, pilot plant or industrial scale.

4. The process according to claim 1, characterized in that it further comprises the following steps:
  a) creating a column in the table, wherein it is indicated that the sample measured by the analytical method contains a response signal, which is outside the range of signals, included in the reference sample analytical reports;
  b) optionally manually or automatically verifying whether this is the system peak or a peak of a new impurity;
  c) including this peak in the reference sample analysis report,
  d) again starting the whole routine in this analytical method (Hash group).

5. The process of claim 1, which is a process for synthesizing a pharmaceutically active substance or for preparing a specific form of a pharmaceutically active substance selected from the group consisting of hydrates, polymorphs, salts or other derivatives.

6. The process of claim 1, wherein for reference samples a correlation between the response signals obtained by use of an analytical method as defined in step (iv) of claim 1 and an attribute of interest is established by means of analytical procedures selected from the group consisting of HPLC-MS, HPLC-MS/MS, HPLC-NMR technique or isolation using HPLC-preparative and/or medium pressure liquid chromatography-preparative methods including synthesis of an impurity or component of interest.

7. The process of claim 6, wherein the response signals are the peaks and relative retention times of a chromatogram and wherein the attribute of interest is the chemical structure of an impurity or other chemical component present in the reference sample(s).

8. The process of claim 7, wherein the chromatogram is obtained by using HPLC.

9. The process of claim 1, wherein the label of a response signal obtained by use of an analytical method as defined in step (iv) is changed when the response signal can be assigned to the same attribute of interest in all the other analytical methods characterized by a unique method code as defined in step (iii) of claim 1.

10. The process of claim 9, wherein the response signal is a chromatographic peak characterized by a specific relative retention time, in particular an HPLC peak, and the attribute of interest is the nature of the impurity or chemical component associated with said peak.

11. The process of claim 1, wherein only those response signals of the analytical results obtained in step (iv) of the process as defined in claim 1 are used in the further steps of the process, in particular multivariate analysis, which signals have been successfully assigned to an attribute of interest in all the analytical methods used.

12. The process of claim 11, wherein the response signal is a chromatographic peak characterized by a specific relative retention time, in particular an HPLC peak, and the attribute of interest is the nature of the impurity or chemical component associated with said peak.

13. The process of claim 1, wherein the pre-determined limit is based on a minimum intensity of a chromatographic peak obtained when using HPLC.

14. The process of claim 13, wherein the limit is determined by the purpose of the process for preparing a sample as defined in step (iv) of claim 1.

15. The process of claim 14, wherein the purpose is selected from the group of reaction screening, reaction optimization, purification screening and purification optimization.

16. A process for optimizing one or more parameters of a process for synthesizing or purifying a chemical compound comprising the automated classification and analysis of data, in which process at least one synthesis or purification process parameter is to be optimized, said process comprising the following steps:
   i) using as an analytical method high pressure liquid chromatography (HPLC);
   ii) determining working parameters and conditions for the selected method, which parameters and conditions have an effect on results obtained by using the selected method;
   iii) assigning to a set of data said set of data including a) the selected method and b) a specific combination of working parameters and conditions used in the analytical experiment a unique analytical method code (Hash value), wherein HPLC is used as the analytical method and wherein the Hash value is changed whenever the change of one of the following parameters exceeds the following limits:
   the pH of mobile phase is changed by more than ±0.3;
   the column temperature is changed by more than ±3° C.;
   an additional organic modifier is introduced in the mobile phase;
   another organic modifier is used;
   the slope of gradient profile is modified by more than ±2%;
   percentage of organic solvent in the mobile phase is changed by more than ±1%;
   the column is exchanged by another one having a different selectivity type;
   when a change in one of the parameters selected from the:
      stationary phase (type and manufacturer);
      composition of mobile phase as characterized by the pH and ionic strength of the buffer used and the type and proportion of an organic modifier, if any;
      column temperature
   causes a change in the relative retention times of more than ±5%.
   iv) conducting the process for synthesizing or purifying said chemical compound to obtain at least one reference sample and at least one or more further samples, in which process the one or more parameters are to be optimized, and conducting the analytical method characterized by said Hash value for the at least one reference sample and the at least one or more further samples;
   v) storing the Hash value and the name of the sample as metadata together with the analytical results obtained in step (iv) as an analytical report;
   vi) automatically extracting by using an extraction template or another extraction process the metadata and further data from the analytical reports and transferring them to an enterprise content management system (ECMS) or other database systems;
   vii) automatically organizing by means of a computer-assisted procedure the results according to the Hash value in the ECMS or any other suitable database system,
   viii) correlating the sets of data characterized by different Hash values on the basis of the reference sample measured for each Hash value, thereby creating a correlation matrix/table;
   ix) using the correlation matrix/table for multivariate analysis of the one or more of the synthesis or purification process parameters of the process resulting in the samples recited in step (iv),
   x) wherein said one or more synthesis or purification process parameters of the process as defined in step (iv) are optimized by using the results of step (ix)); and
   xi) synthesizing or purifying the chemical compound using the process and the one or more parameters which have been optimized.

17. The process according to claim 16, wherein the synthesis or purification process parameter to be optimized in selected from the group consisting of amounts and ratios of starting compounds or intermediates used in a chemical reaction, type and amount of solvents used in a chemical reaction, pressure, temperature, the use of an inert gas atmosphere, the time period of using a chemical or physical operation.

18. The process according to claim 16, wherein the synthesis or purification process parameter to be optimized is selected from the group consisting of amounts and ratios of starting compounds or intermediates used in a chemical reaction, type and amount of solvents used in a chemical reaction, pressure, temperature, the use of an inert gas atmosphere, the time period of using a chemical or physical operation.

19. A method of optimizing a chemical process for producing or purifying a chemical compound, the method comprising:
  i) determining a set of parameters and conditions for an analytical method to analyze a set of properties of the chemical compound, wherein the set of parameters and conditions have an effect on an analytical result obtained using the analytical method;
  ii) creating a data set identifying the analytical method and the set of parameters and conditions for the analytical method, and assigning Hash value to the data set;
  iii) conducting the process for synthesizing or purifying the chemical compound to obtain at least one reference sample and at least one or more further samples, in which process at least one parameter is to be optimized, and using an analytic device to perform the analytical method identified by the Hash value for the at least one reference sample and the at least one or more further samples to generate the analytical result;
  iv) storing in a computer as an analytical report a set of metadata, including the Hash value and a sample name, and the analytical result;
  v) repeating prior steps i) through iv) using one or more different sets of parameters and conditions to generate one or more additional analytic reports;
  vi) automatically extracting by the computer the sets of metadata from the analytical reports;
  vii) automatically organizing by the computer the analytical results from the analytical reports according to the Hash values;
  viii) automatically creating by the computer a correlation table correlating the analytical results based on the reference samples;
  ix) automatically performing by the computer a multivariate analysis on the sets of parameters and conditions contained in the correlation table to generate a result; and
  x) adjusting at least one parameter or condition of the chemical process based on the result and then synthesizing or purifying the chemical compound using the process and the at least one parameter which has been optimized.

* * * * *